United States Patent [19]

Suzuki

[11] Patent Number: 4,566,792
[45] Date of Patent: Jan. 28, 1986

[54] MULTI-CHANNEL SPECTROPHOTOMETRIC MEASURING DEVICE

[75] Inventor: Jugoro Suzuki, Kyoto, Japan
[73] Assignee: Shimadzu Corporation, Kyoto, Japan
[21] Appl. No.: 463,961
[22] Filed: Feb. 4, 1983
[51] Int. Cl.$^4$ ............................. G01J 3/18; G01J 3/42
[52] U.S. Cl. ..................................... 356/319; 356/328
[58] Field of Search ............... 356/319, 323, 325, 326, 356/328

[56] References Cited

U.S. PATENT DOCUMENTS

| | | | |
|---|---|---|---|
| 3,880,523 | 4/1975 | Thomas | 356/328 X |
| 3,985,441 | 10/1976 | Schoeffel et al. | 356/325 X |
| 4,259,014 | 3/1981 | Talmi | 356/328 |

FOREIGN PATENT DOCUMENTS 53-122474 10/1978 Japan .

Primary Examiner—F. L. Evans
Attorney, Agent, or Firm—Brumbaugh, Graves, Donohue & Raymond

[57] ABSTRACT

The disclosure is directed to a spectrophotometric measuring device equipped with a plurality of channels which automatically analyze many specimens with different testing items in a short period of time for application in biochemical automatic analysis or the like. The device of the invention is characterized in that white light from one light source is subjected to spectral diffraction through a long slit in X direction and wavelength dispersion irradiation light of an optical system including a spectroscope for dispersing spectrum of monochromatic light in Y direction intersecting at right angles with the slit, is projected onto one plate surface so as to select positions of the plate surface in the Y direction and X direction, and by providing the incident end faces of the optical fibers on the selected positions for free change-over, monochromatic lights of arbitrary wavelengths determined by the respective testing items are taken out, while the sample cell and detector are disposed to confront the optical fiber incident end faces for detection of intensity of light transmitting through the sample cell.

4 Claims, 5 Drawing Figures

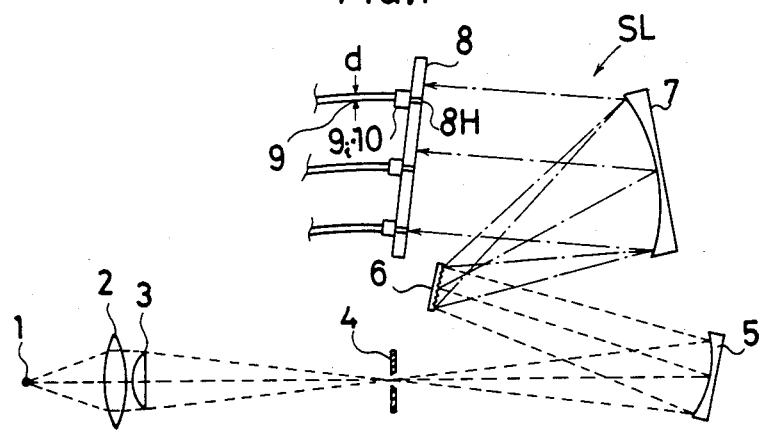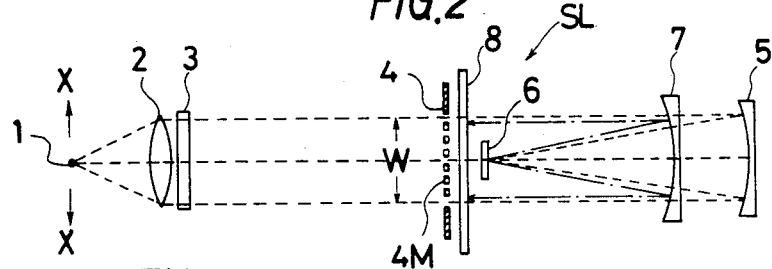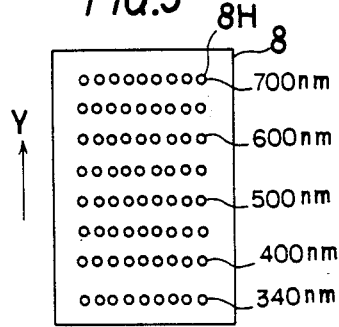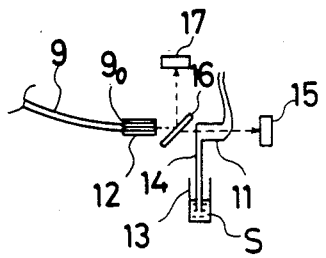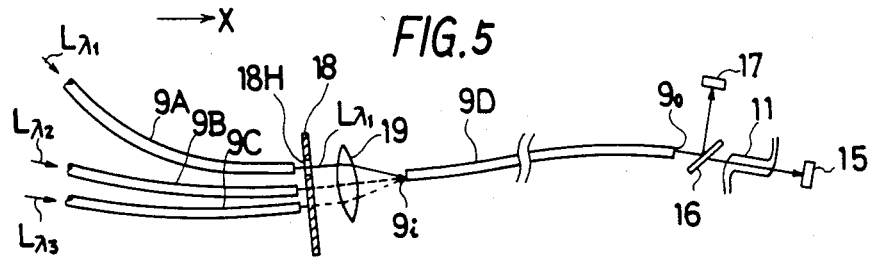

MULTI-CHANNEL SPECTROPHOTOMETRIC MEASURING DEVICE

BACKGROUND OF THE INVENTION

1. Field of the Invention

The present invention relates to a multi-channel spectrophotometric measuring device for simultaneous analysis of a large number of specimens with different items to be tested, to be applied for example, in a field such as biochemical automatic analysis or the like.

2. Description of the Prior Art

Recently, owing to the rapid increase in the number of specimens to be dealt with, arising from greater importance attached to clinical examinations, there has been an increasing demand for labor saving and simultaneous analysis of many items, with various methods being developed for the purpose, as for example, a multi-channel two wavelength spectrophotometer disclosed in Japanese Laid Open Patent Application Tokkosho 53-122474, which has come to be employed in a wide range of applications. The spectrophotometer referred to above is so arranged that transmitting light from a large number of sample cells (flow cells in this case) arranged in the direction of an X axis is focused in a slit elongated in the same X axis direction, and is then subjected to spectral analysis by a diffraction grating or the like so as to be projected onto a wavelength dispersion optical system disposed in such a manner that the spectral range of light transmitted through each cell and subjected to the spectral diffraction becomes spectrum dispersed in the direction of a Y axis. Also there is provided a light receiving portion of the spectrum for the above monochromatic light, and this light receiving portion has a detecting portion including more than two detecting elements disposed in the Y direction, with the respective detecting portions being arranged in a plate-like configuration in the X axis direction so as to correspond to the positions where the respective spectral bands appear.

By the conventional arrangement as described above, selection and combination of reference wavelength and sample wavelength to be determined by the examination items of the specimens are facilitated making it possible to allow simultaneous analysis of many specimens, but owing to the necessity of maintaining an optical path length required for the analysis, since the flow cells are disposed to intersect at right angles with respect to the irradiation optical axis, the diameter of the flow cell cannot be excessively reduced, and due to the fact that the position of the flow cell is restricted to the predetermined position of the above optical system, the length of the sample suction flow path, for example, in order to successively introduce a reagent separately poured into the specimens from containers of the reaction samples into the flow cell, cannot be reduced beyond a predetermined length, and consequently, extra samples are required for eliminating such carry-over, thus resulting in the disadvantage that sufficient analysis cannot be effected on samples of small quantity.

SUMMARY OF THE INVENTION

Considering the foregoing, an essential objective of the present invention is to provide an improved multi-channel spectrophotometric measuring device which is so arranged that, by fixing light incident end portions of optical fibers onto a monochromatic spectrum forming surface of a wavelength dispersion optical system of conventional arrangement so as to be changed-over as desired, light with arbitrary wavelengths to be determined by the testing items is taken out to be transmitted through said optical fibers to any required position, as for example, to a position of a flow cell provided immediately above the sample container containing the reaction sample whereby firstly, selection of wavelengths is facilitated, and secondly, the flow cell may be elongated into a compact size by arranging light incidence upon the flow cell, as for example, in the direction of the sample flow path, while the flow path for introducing the sample into the flow cell may be shortened so as to make it possible to effect analysis with samples in a small amount without carry-over.

BRIEF DESCRIPTION OF THE DRAWINGS

FIG. 1 is a meridional plane diagram of an optical system for a multi-channel spectrophotometric measuring device according to one preferred embodiment of the present invention, FIG. 2 is a sagittal plane diagram of the above optical system, FIG. 3 is a top plan view showing one example of an optical fiber fixing plate at a monochromatic spectrum forming surface, FIG. 4 is a schematic diagram showing the relation among the optical fiber light emitting end portion, flow cell, and detection elements for a double beam light measurement in the device of FIG. 1, and FIG. 5 is a schematic diagram showing the construction of a wavelength selecting portion in the case where the above device is applied to a multi-wavelength light measurement.

(SL)—Wavelength dispersion optical system
(1)—white light source, (2),(3)—condenser lenses,
(4)—inlet slit (with stray light prevention mask),
(5),(7)—spherical mirrors, (6)—dispersing element,
(8)—monochromatic spectrum forming surface (optical fiber fixing plate),
(8H)—hole in the optical fiber fixing plate,
(9)—optical fiber,
(9i)—incidence end portion of the optical fiber,
(9o)—light emitting end portion of the optical fiber,
(11)—sample cell (flow cell),
(12)—selfoc lens,
(16)—half mirror, (15),(17)—optical detectors
(18)—wavelength selector, (S)—sample

DETAILED DESCRIPTION OF PREFERRED EMBODIMENT

Referring now to the drawings, one preferred embodiment of the present invention will be described hereinbelow.

FIG. 1 shows a meridional plane diagram of a dispersion optical system (SL) as viewed from the front side of the measuring device according to one preferred embodiment of the present invention, while FIG. 2 is a sagittal plane diagram of the same dispersion optical system (SL) as observed from the top face of the device.

As shown in FIGS. 1 and 2, the multi-channel spectrophotometric measuring device according to the present invention includes a white light source (1), a spherical lens (2) and a cylindrical lens (3) disposed adjacent to each other in a light path of the light source (1), and an inlet slit (4) disposed in the light path subsequent to the cylindrical lens (3), all of which constitute an optical system for condensation of the light from said light source (1). Although the inlet slit (4) may be formed into an elongated slit corresponding to a width (W) of light flux in FIG. 2, it is formed into slits in the form of holes laterally (i.e. in an X direction in the embodiment) arranged as shown in FIG. 2 for the prevention of stray light, with (4M) forming a mask. The device further includes spherical mirrors (5) and (7), a dispersing element (6) such as a diffraction grating or prism, etc., an optical fiber fixing plate (8) of a magnetic material provided at the monochromatic spectrum forming surface, and formed therein with a plurality of holes (8H), and optical fibers (9) as illustrated. Since the optical fibers (9) are each provided, for example, with a ferrite magnet (10) at each light incident end portion (9i) thereof, their fixed positions may be readily altered as desired.

Referring also to FIG. 3, there is shown one example of the optical fiber fixing plate (8), in which holes (8H) are formed, for example, in eight rows in the Y axis direction, and in nine rows in the X axis direction, while the respective rows in the Y axis direction are sectioned by the mask (4M) of the slit (4), with those in the X axis direction corresponding to ones of the same wavelengths of the appearing spectrum. More specifically, the eight rows in the Y axis direction are arranged to correspond, for example, to approximately each 50 μm of the wavelengths ranging from 700 nm to 340 nm. Although the automatic analysis for as many as twenty channels can be effected by the optical fiber fixing plate (8) as described above, the eight rows in the Y axis direction may further be increased in number by several more rows so as to correspond, for example, to intermediate wavelengths such as 670, 628, 574, 415 nm - - - and so forth. The optical fibers (9) which are each arranged to be fixed into the plurality of holes (8H) of the fixing plate (8) as described above through attraction by the magnets (10) at the end portions (9i) thereof, need not be provided for all of the seventy-two holes (8H) shown, for example, in FIG. 3, but the number thereof relates to the number of flow cells (11) provided at the detecting portion to be subsequently described, and, in the case of one wavelength light measurement, for example, may be equivalent to the number of flow cells, i.e. the number approximately equal to the number of channels to be dealt with. Meanwhile, in the case of multi-wavelength light measurement of more than two wavelengths, the optical fibers (9) may be provided so as to correspond in number to the number obtained through multiplication of the above number of channels by the number of the wavelengths, etc., and thus, the number of the optical fibers (9) may be altered to a large extent according to the employed purpose.

Reference is also made to FIG. 4 showing a diagram illustrating the construction of the detecting portion which is arranged to project an arbitrary monochromatic light transmitted by the optical fibers (9) into the flow cell (11) for detection of intensity of the transmitted light.

The arrangement as shown in FIG. 4 includes a fiber lens (12) in a bundled configuration made of a material generally called "selfoc" lens (name used in trade) or rod lens, and provided at the light emitting ends (9O) of the optical fibers (9), and, by providing the above fiber lens (12), the focal length and converged light spot diameter, etc. of the projected light may be set as desired. Furthermore, by providing the above lens (12) at the incident end portions (9i) of the optical fibers (9) as shown in FIG. 1, the external diameter (d) of the optical fibers (9) can be reduced, thus resulting in the improvement of flexibility, and facilitation of manufacture of the device. There is provided a reaction tube (13) which is carried to a position immediately below the flow cell (11) upon completion of reaction of the sample (S) so that the sample (S) is sucked into the flow cell (11). Since a suction tube (14) may be made extremely short as described above, cleaning of the inner wall of the tube can be sufficiently effected even by a very slight amount of the sample, thus constituting the feature that the sample necessary for analysis may be of small quantity. Owing to the configuration of the flow cell (11) placed lengthwise in the direction of the optical axis, a compact sized one with diameter in the range of 1.5 to 2 mm may be employed at a light path length of about 10 mm. Further provided is a light detection element (15), as for example, a photo-diode or the like, which is employed for detecting intensity of light transmitting through the sample within said flow cell. In the case of one wavelength, two wavelength or multi-wavelength single beam light measurement, the detection element (15) alone may be sufficient for the purpose, but when double beam light measurement method is to be employed, a half mirror (16) is provided between the optical fiber projecting end portion (9O) and the flow cell (11), and the intensity of ½ of the emitted light is detected by another light detecting element (17). By the above arrangement, the variation in the light transmitting characteristics of the optical fibers (9) can be corrected for improving the measuring accuracy. The half mirror as described above may be of simple glass. FIG. 5 is a diagram showing a wavelength selector portion which is so arranged that, in the case of the above multi-wavelength light measurement of more than two wavelengths as described above, a plurality of monochromatic light $(L\lambda_1)$, $(L\lambda_2)$, $(L\lambda_3)$ - - - and so forth, having different wavelengths is taken out of the optical fiber fixing plate (8) as shown in FIG. 3 and thereafter, selectively directed into the sample. Now, the monochromatic lights $(L\lambda_1)$, $(L\lambda_2)$, and $(L\lambda_3)$ respectively having different wavelengths are transmitted from the optical system described earlier to the front face of a sector (18) by the optical fibers (9A), (9B) and (9C). The sector (18) is subjected to rotation or reciprocating movement by a mechanism (not shown) so as to project only the light having any one wavelength of the above three wavelengths (the figure shows the case of $L\lambda_1$) into the incident end portion of the one optical fiber (9D) via the hole (18H) thereof and through the condenser lens (19). The structure after the light emitting end portion of the optical fiber (9D) is the same as in FIG. 4. There may be cases where the selfoc lens (12) disposed at the light emitting end portion is not provided. As described above, by successively directing $(L\lambda_2)$ and $(L\lambda_3)$ into the flow cell (11) and detecting the transmitting light intensity thereof, it becomes possible to effect the multi-wavelength light measurement through combination of arbitrary wavelengths. The construction in FIG. 5 corresponds to one flow cell, and as a device, for example, if the flow cells are provided by the number of rows of different wavelengths in the Y axis direction as shown in FIG. 3, the specimen information for the flow cells in that number may be simultaneously obtained. The multi-wavelength light measuring method as referred to above is suitable for obtaining specimen information such as hemolysis, turbidity, high bilirubin, etc.

Described so far is the embodiment according to the present invention which explains the respective elements of the multi-channel spectrophotometric measuring device, and it is needless to say that the present invention may be applied to a single channel one wavelength spectrophotometric device. It should also be noted that the present invention is not limited in its application to the drawings and description given in the foregoing, and for example, the optical fiber fixing plate may be made of a transparent plate, if the fixing means at the optical fiber incident end portion is properly altered, with complete freedom of the selection of wave lengths, etc. being achieved thereby.

What is claimed is:

1. A multi-channel spectrophotometric measuring device comprising:

a source of white light, a slit plate provided with a slit extending in the X direction, an optical system disposed between said source of white light and said plate for converging the white light from said light source through said plate, spectral diffraction means for dispersing the light that travels through said slit plate into a spectral band, an apertured plate having a front face and rear face for receiving on said front face thereof said spectrum band, an array of holes through said plate for the passage therethrough of substantially monochromatic light of certain wavelengths, said array of holes including a plurality of rows of holes, the holes of each row being spaced apart in the X direction along substantially the same band of the spectrum for the passage of substantially monochromatic light of the same wavelength and the rows being spaced apart in the Y direction so that the holes of different rows permit passage of substantially monochromatic light of different wavelengths, a plurality of optical fibers for transmitting each substantially monochromatic light of different wavelength, the incident ends of said fibers being detachably mounted onto said holes provided on said rear face of said apertured plate, a sector having a front face and rear face arranged with said front face facing the light emitting ends of the plurality of optical fibers for selectively transmitting each monochromatic light of different wavelength, a separate optical fiber arranged on the side of said rear face of said sector for transmitting the substantially monochromatic light, a separate optical system disposed between said sector and said separate optical fiber for directing the substantially monochromatic light selectively transmitted through said sector towards said separate optical fiber, a sample cell at the light emitting end of said separate optical fiber, and detector means for detecting the intensity of the light transmitted through said sample cell.

2. A multi-channel spectrophotometric measuring device as set forth in claim 1 including a fiber lens at the light emitting end of said separate optical fiber.

3. A multi-channel spectrophotometric measuring device as set forth in claim 1 including a half mirror disposed between the light emitting end of said separate optical fiber and the sample cell and arranged at an angle of 45° to the optical axis of the light emitted from said light emitting end, and another detector on the optical axis of the light partially reflected at right angles to the optical axis of the light transmitted through said half mirror.

4. A multi-channel spectrophotometric measuring device as set forth in claim 1 including a mask for said slit plate for directing the light in a forward direction.

* * * * *